United States Patent
Gao et al.

(10) Patent No.: US 6,791,280 B2
(45) Date of Patent: Sep. 14, 2004

(54) SYSTEM AND METHOD FOR GENERATING A DISCHARGE IN HIGH PRESSURE GASES

(75) Inventors: Ju Gao, Champaign, IL (US); Joseph T. Verdeyen, Savoy, IL (US)

(73) Assignee: Advanced Lighting Technologies, Inc., Solon, OH (US)

( * ) Notice: Subject to any disclaimer, the term of this patent is extended or adjusted under 35 U.S.C. 154(b) by 0 days.

(21) Appl. No.: 10/112,349

(22) Filed: Apr. 1, 2002

(65) Prior Publication Data

US 2002/0140374 A1 Oct. 3, 2002

Related U.S. Application Data

(60) Provisional application No. 60/279,684, filed on Mar. 30, 2001.

(51) Int. Cl.[7] ............................ H05B 41/36; H01J 19/80
(52) U.S. Cl. ..................................... 315/224 R; 315/39
(58) Field of Search .................. 315/39, 39.51, 315/39.61, 39.71, 40, 224, 241 R

(56) References Cited

U.S. PATENT DOCUMENTS

| | | | | |
|---|---|---|---|---|
| 5,175,476 A | * | 12/1992 | Anderson et al. | 315/248 |
| 5,306,987 A | * | 4/1994 | Dakin et al. | 315/248 |
| 5,438,235 A | * | 8/1995 | Sommerer et al. | 313/489 |
| 5,519,285 A | * | 5/1996 | Ukegawa et al. | 313/594 |
| 5,841,243 A | * | 11/1998 | Hooper | 315/248 |
| 6,100,650 A | * | 8/2000 | Yokozeki et al. | 315/248 |
| 6,127,275 A | * | 10/2000 | Flamm | 438/710 |
| 6,483,259 B1 | * | 11/2002 | Kramer | 315/291 |

* cited by examiner

Primary Examiner—Don Wong
Assistant Examiner—Minh Dieu A
(74) Attorney, Agent, or Firm—Duane Morris LLP

(57) ABSTRACT

A method of generating an electrical discharge in a high pressure gas contained in a sealed enclosure. The method includes driving a helical coil resonator at an RF frequency to generate an RF electric-magnetic field sufficient to generate an electrical discharge in the high pressure gas. The electrical discharge produces an emission spectrum that may be spectroscopically analyzed to determine the composition and impurity content of the gas.

52 Claims, 4 Drawing Sheets

SYSTEM AND METHOD FOR GENERATING A DISCHARGE IN HIGH PRESSURE GASES

RELATED APPLICATIONS

This application claims the benefit of U.S. Provisional Patent Application No. 60/279,684 filed Mar. 30, 2001.

FIELD OF THE INVENTION

The present invention relates to gas composition analysis. More particularly the present invention relates to nondestructive analysis of high pressure gas contained in dielectric enclosures by emission spectroscopy.

BACKGROUND OF THE INVENTION

Metal halide and other high intensity discharge (HID) lamps have found widespread acceptance for lighting large area indoor and outdoor spaces. In the manufacture of HID lamps, it is often desirable to provide a controlled atmosphere for many of the components of the lamp to prevent premature failure of the components and thereby prolong the operating life of the lamp. For example, the exposure of the arc tube of an HID lamp to small amounts of oxygen during lamp operation will significantly degrade the components leading to lamp failure, thus shortening the operating life of the lamp. Further by way of example, the exposure of the arc tube to hydrogen may lead to diffusion of hydrogen into the arc tube leading to high starting and re-ignition voltages, and ultimately reduced life expectancy of the lamp. To prevent the exposure of such components to damaging atmospheres, it is well known to provide a controlled atmosphere for the components by enveloping the components in a desired atmosphere contained within an outer lamp jacket. Typically, the outer jacket of an HID lamp is filled with an inert gas such as nitrogen.

In view of the deleterious effects of the presence of impurities, it is desirable to nondestructively analyze the composition and impurity content of the gaseous atmosphere contained within the lamp outer jackets. Gas analysis by emission spectroscopy is well known in analyzing the composition and impurity content of gaseous atmospheres at low pressures (<about 0.1 atm). However, the gaseous atmosphere contained within an outer jacket of an HID lamp is typically at relatively high pressure (about 0.1–2.0 atm). There remains a need for nondestructive gas analysis by emission spectroscopy in high pressure gaseous atmospheres.

Accordingly, it is an object of the present invention to obviate the deficiencies of the prior art and to provide a novel system and method for nondestructive high pressure gas analysis.

It is another object of the present invention to provide a novel system and method for generating a discharge in a high pressure gas.

It is a further object of the present invention to provide a novel system and method for creating a stable electrical discharge in a high pressure gas contained in a sealed enclosure, so that the composition and impurity content of the gas can be spectroscopically analyzed without destroying the enclosure.

It is yet another object of the present invention to provide a novel system and method for emission spectroscopy of gaseous atmospheres.

It is yet another object of the present invention to provide a novel system and method for nondestructive analysis of HID lamps.

These and many other objects and advantages of the present invention will be readily apparent to one skilled in the art to which the invention pertains from a perusal of the claims, the appended drawings, and the following detailed description of the preferred embodiments.

DETAILED DESCRIPTION OF THE INVENTION

The present invention generally finds utility in generating a discharge in high pressure gas. By way of example only, certain aspects of the invention will be described in connection with emission spectroscopy for nondestructive analysis of the gaseous content in HID lamps.

According to one aspect, the present invention provides a high Q, single frequency RF discharge source for generating a small localized and stable electrical discharge (plasma) in a high-pressure (0.1 atm to 2 atm) gas contained within the outer jacket of an HID lamp. The discharge source includes a helical coil resonator (HCR) for providing sufficient RF energy to generate the discharge. The optical emission spectrum from the plasma can then be spectroscopically analyzed to determine the composition of the gas and the gaseous impurity content within the enclosure. Impurity concentrations less than about 0.01 percent by volume may be detected. Typically the gaseous atmosphere comprises $N_2$, and may include gaseous impurities such as $O_2$, $H_2$, $CO_2$, CO, $H_2O$, $CH_4$, and the like, which contain elements such as O, H, C, and/or any combinations thereof. The RF discharge source of the present invention is capable of establishing and maintaining a discharge in high pressure gas, and consumes very little power, thus being useful in both lab and production line applications.

The RF discharge source creates an electrical discharge inside the enclosure by generating an RF electric-magnetic (electric) field that penetrates through the dielectric wall of the enclosure. The electric field required for the discharge is proportional to E/N, where E is the electric field strength and N the number density of the gas. The gas pressure inside the outer jacket of a HID lamp is typically about 0.5 atm at room temperature, requiring a field strength of about 7 kV/cm to establish a discharge. When a discharge is established, the heat generated by the discharge reduces the gas number density (N) thus requiring less electric field strength (E) to maintain the discharge.

The optical emission spectrum of the plasma, i.e., the atomic and molecular emission of species in the excited plasma, is analyzed using conventional spectroscopic techniques to determine the composition and impurity content of the high pressure gas in the enclosure. This typically involves recording the optical emission spectrum of the plasma at UV, visible, and near-IR wavelengths at sufficiently high resolution to resolve the atomic lines of the impurities of interest. The spectrum is analyzed by visual/ graphical and/or computer aided data manipulation to measure the magnitude of the spectral peaks of interest. This data is compared to similar data collected from known standards of the impurities of interest. The concentrations of the impurities are then calculated by comparison to the known standards.

Figure 1:
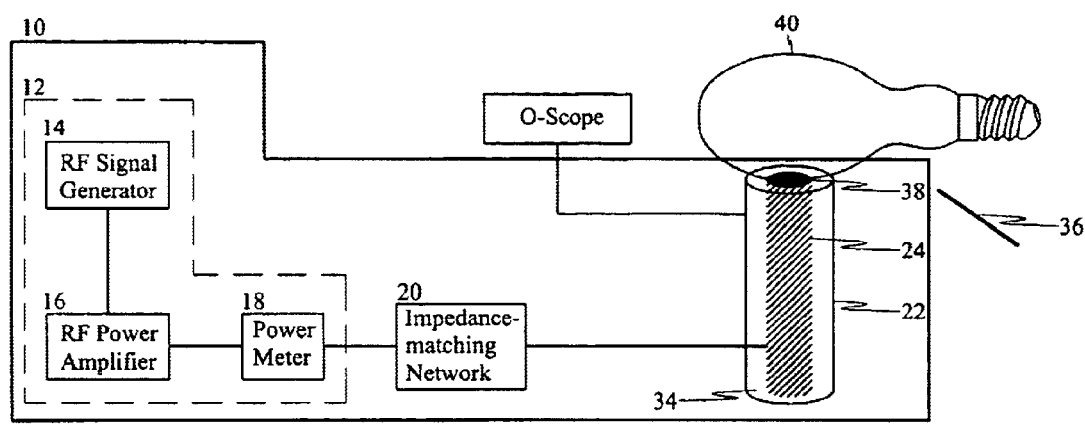
FIG. 1 is a schematic diagram illustrating an RF discharge source according to an exemplary embodiment of the present invention.

FIG. 1 schematically illustrates the RF discharge source 10 according to an exemplary embodiment of the present invention. The RF discharge source 10 is capable of producing the several thousand volts needed to strike a discharge in a high pressure gas contained in a sealed enclosure. The RF discharge source 10 comprises an RF power generator 12, an impedance-matching network 20, and an HCR 22. The RF power generator 12 includes an RF signal generator 14, an RF power amplifier 16, and power meter 18. The RF power generator 12 typically outputs about a few hundred volts and drives the HCR 22 at RF frequencies from about 100 kHz to greater than 100 MHz, and typically about 10 MHz. The HCR 22 operates like a combination of an open-circuited quarter-wave transmission line in parallel with an inductor back to ground to step up the voltage from the RF power amplifier 16 by factors of 20 to 100 or greater.

Figure 2:
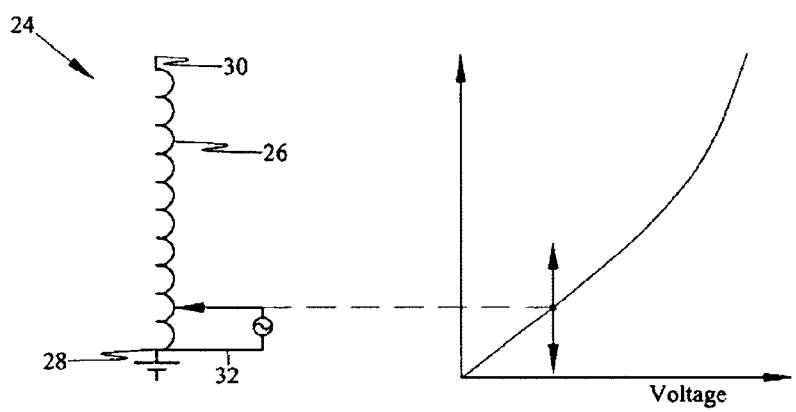
FIGS. 2 and 3 are schematic diagrams illustrating an exemplary helical coil resonator.

The HCR 22 typically includes a wire helix 24 and an electrically conductive shield 34. As illustrated in FIG. 2, the wire helix 24 is formed by a conductive spiral coil 26 having a first end 28 connected to ground and a second opposing end 30 serving as an electrode. An input tap 32 is located on the coil 26 between the ground (the first end of the coil 28) and a point close to the ground.

Referring again to FIG. 1, the enclosure or outer jacket 40 to be analyzed is placed in contact with the electrode 30 where the RF voltage is highest. The RF electric field penetrates through the dielectric wall of the enclosure 40 to generate a very stable discharge inside the enclosure 40. A discharge within the outer jacket of an HID lamp may be generated without exciting the gaseous contents of the arc tube (not shown), which typically contains a low pressure gas such as Ar and a low pressure vapor such as Hg. The high voltage at the electrode 30 is a result of the RF power injected at a tap close to the ground point. In one embodiment, a fiber optic light gathering device 36 collects the optical emission spectrum of the plasma in the UV, visible, and near IR wavelength ranges, for analysis.

As discussed above, the operation of the HCR 22 is similar to a transformer, with the voltage being stepped up by the turns ratio of the coil 26. However, the operation of the HCR 22 is frequency dependent, and its operation may best be modeled by a transmission line cavity having a wire length L in the coil (illustrated in FIG. 2 measured from the tap point or first end 28 of the coil 26 to the electrode or second end 30 of the coil 26) being slightly less than one quarter of an RF wavelength. In one embodiment of the present invention, a coil length L of about 5.5 meters is suitable for an operating frequency of about 13.6 MHz (which is set to operate within the allowable FCC bandwidth). It should be understood that the coil length and operating frequency are not limited to these values.

Figure 3:
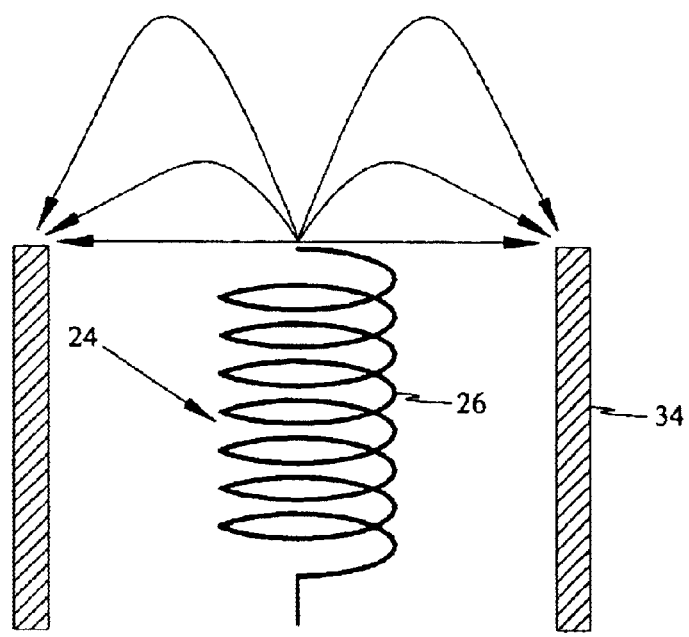

The electrically conductive shield 34 is typically formed from metal to enclose the coil 26 as illustrated in FIG. 3 and provides the return path for the RF current. The combination of the RF shield 34, coil, and the selection of the tap point 32 enable the HCR 22 to exhibit a Q of between about 500 and about 900.

Referring again to FIG. 2, the input signal is connected to the input tap 32 between the ground and a point close to the ground. Since the total coil length L is about one quarter of the wavelength of the RF electric field, the highest electric field strength is located at the electrode 30 formed by the other end of the coil 26. The electric field strength may be raised or lowered by raising or lowering the electric field strength at the input tap 32.

The impedance-matching network 20 matches the input impedance of the HCR 22 to the output impedance of the RF power generator 12 at the frequency of operation. In one embodiment, the matching impedance may be about 50 ohms. At RF frequencies, the input impedance contains both resistance and reactance. The matching network 20, made up of inductance and capacitance, may be designed to modify the HCR input impedance to be about 50 ohms. Moreover, the location of the input tapping point 32 should also be considered in matching the input impedance of the HCR 22 to the output impedance of the RF power generator 12.

Figure 4:
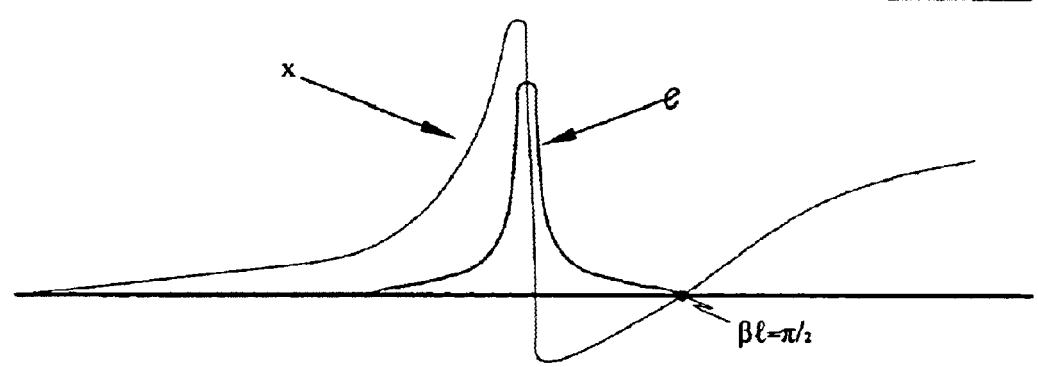
FIG. 4 is a graph illustrating the impedance of a helical coil resonator as a function of frequency at the driving point.

Specifically, the open-circuit coil can be viewed as an open-circuit transmission line that is about one quarter wavelength in length. Since the coil 26 is open circuited, the driving point impedance $Z_d$ of the open part of the circuit is approximately:

$$Y_d = +j\, Y_0 \tan \beta l, \quad Z_d = -j\, Z_0 \cot \beta l$$

where $Y_0 = 1/Z_0$, $Z_0$=characteristic impedance of the helical transmission line, 1 is the length from the driving point to the tip of the electrode, and $\beta$ is the phase constant. The impedance as a function of frequency at the driving point is measured and plotted in FIG. 4. This $Z_d$ contains both the real part and imaginary parts. In order to match the output impedance of the RF source (50 ohms), a properly-designed impedance matching network that consists of capacitors and inductors is inserted between the RF source and the driving point of the HCR to obtain the maximum delivery of power of the RF source to the HCR.

The RF discharge source 10 may be operated by first adjusting the frequency of the RF signal 14 generator to match the resonant frequency of the HCR 22. Alternatively the tap point, coil spacing or other dimensions of the HCR 22 can be adjusted to match the (fixed) frequency of the RF signal generator 14. In one embodiment, the combination of the RF signal generator 14 and RF power amplifier 16 of the RF power generator 12 produces a sinusoidal voltage of about 300 Volts (rms). The power generated at the output of the amplifier 16 passes through the power meter 18, which is capable of measuring both forward and reflected wave powers.

The power subsequently goes through the matching network 20 before it couples to the HCR 22. The matching network 20 includes a variable capacitor (not shown) which allows the matching impedance of the matching network 20 to be selectively adjusted by tuning the capacitor in order for the electrode 30 of the coil 26 to reach its highest voltage. The impedance matching network 20 is adjusted to minimize reflected power and maximize "forward" power into the plasma load and to maximize the physical and temporal stability of the plasma.

An electric field pick-up device 38 may be provided to monitor the electrode voltage. The electric field pick-up device 38 includes a metal plate soldered to the center conductor of a coaxial connector positioned near the electrode 30. In one embodiment, the signal from the capacitance pickup may be used to maximize the voltage at the electrode 30 as the matching network components are changed.

It may be necessary in some instances to reduce the heating effect of the RF discharge on the dielectric surface of the enclosure containing the gas to be analyzed. The RF signal generator 14 may include a gate feature that allows an RF waveform to be duty-cycle modulated. A suitable modulation frequency may be between 10 and 1000 Hz, and typically about 120 Hz, and a duty cycle between 1 percent and 99 percent, and typically about 10 percent. The pulsed RF discharge reduces the heating effect of the discharge on dielectric enclosure. In addition to reducing the duty cycle of the continuous RF waveform, the gated RF allows analysis of optical emission from excited atoms or molecules which persist and radiate in the afterglow during the period when the RF source is gated to the "off" state.

In embodiments of the present invention for generating a discharge in gases at pressures over about 300 torr, a Tesla coil (not shown) has been found to be suitable for initiating the discharge.

EXPERIMENTAL RESULTS

Figure 5:
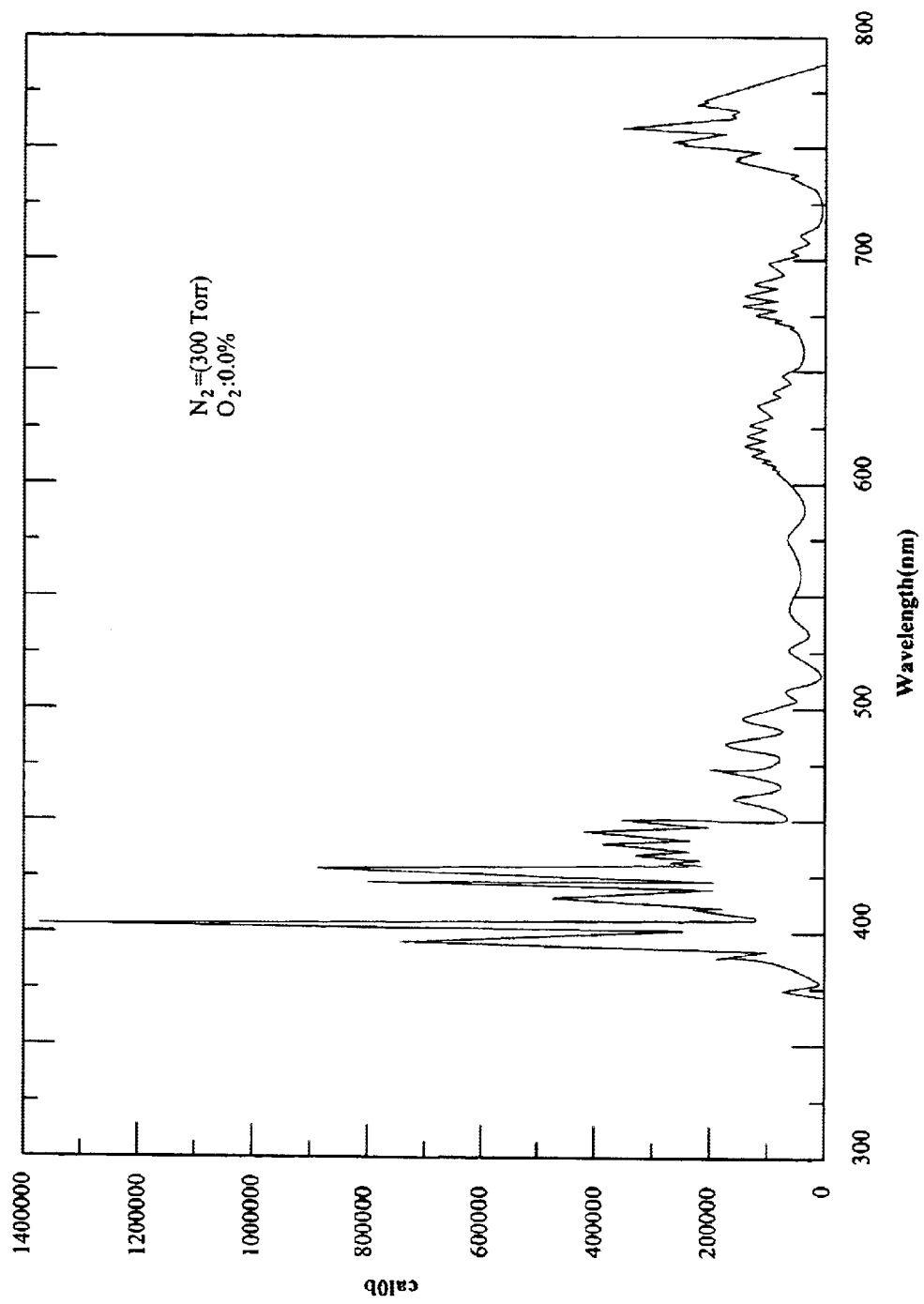
FIG. 5 is a graph illustrating a spectrum from a discharge in pure $N_2$ gas at 0.3 atm (300 torr).
Figure 6A:
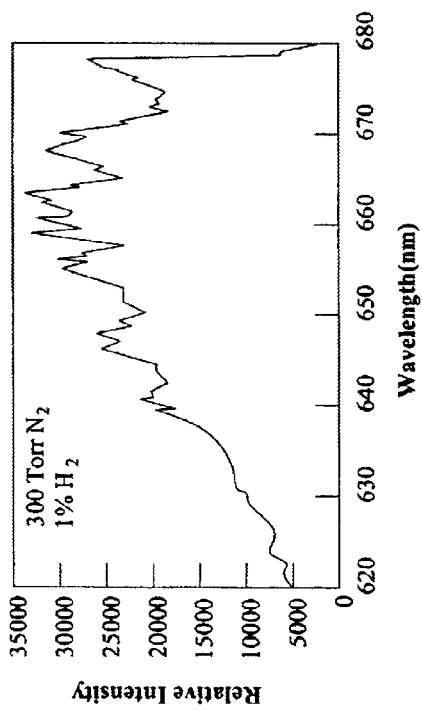
FIG. 6A is a graph illustrating a typical emission spectrum from a helical coil resonator RF discharge in $N_2$ gas and 1 percent hydrogen at 0.3 atm (300 torr).
Figure 6B:
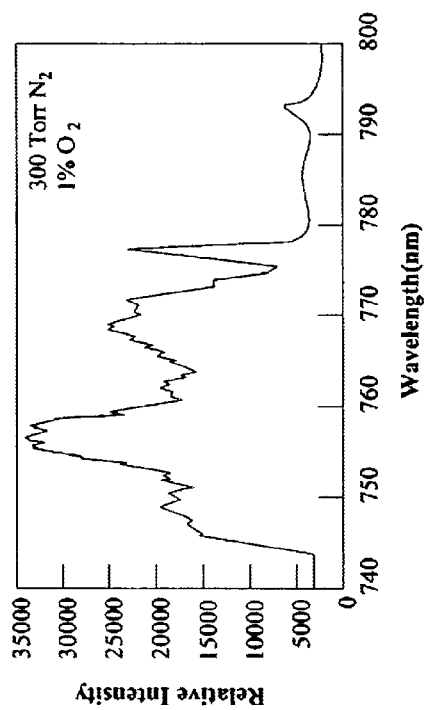
FIG. 6B is a graph illustrating a typical emission spectrum from a helical coil resonator RF discharge in $N_2$ gas and 1 percent oxygen at 0.3 atm (300 torr).

Emission spectra were recorded using an Acton Spectra-Pro 300i spectrophotometer over a range of 350 nm to 900 nm with a resolution of 0.4 nm FIG. 5 illustrates a spectrum from a discharge in pure $N_2$ gas at 300 torr. FIG. 6A illustrates the analytically useful lines of atomic hydrogen (656 nm) and FIG. 6B illustrates the analytically useful lines of atomic oxygen (777 nm) from standards of known 1% hydrogen and 1% oxygen in nitrogen at 300 torr. These atomic lines can be seen as relatively sharp peaks superimposed on the complex nitrogen molecular band spectra. Detection limits for oxygen and hydrogen in a fill comprising nitrogen at 500 torr include about 0.3% and 0.1% by volume respectively.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. A method of generating an electrical discharge in a high pressure gas contained in a sealed enclosure, the method comprising the steps of:
    contacting a helical coil resonator with a dielectric wall of the enclosure; and
    driving the helical coil resonator at an RE frequency to generate an RE electric-magnetic field to thereby generate an electrical discharge in the high pressure gas.

2. The method according to claim 1, wherein the pressure of the gas is between about 0.1 atm and about 2.0 atm.

3. The method of claim 1, wherein the pressure of the gas is about 0.5 atm.

4. The method of claim 1, wherein the RE frequency is about 10 MHz.

5. The method of claim 1, wherein the RE frequency is between about 10 MHz and about 100 MHz.

6. The method of claim 1, wherein the RE frequency is greater than about 100 MHz.

7. The method of claim 1, wherein the RE frequency is between about 100 kHz and about 10 MHz.

8. The method of claim 1, wherein the RE electric-magnetic field generated in the driving step nondestructively penetrates the dielectric wall of the enclosure.

9. The method of claim 1, wherein the driving step includes pulsing the RE electric-magnetic field to nondestructively penetrate the dielectric wall of the enclosure.

10. The method of claim 9, wherein the pulsing of the RE electric-magnetic field is performed at a frequency of between about 10 Hz and about 1000 Hz.

11. The method of claim 10, wherein the pulsing of the RF electric-magnetic field is performed at a frequency of about 120 Hz.

12. The method of claim 9, wherein the pulsing of the RE electric-magnetic field has a duty-cycle between about 5 percent and about 20 percent.

13. The method of claim 12, wherein the pulsing of the RE electric-magnetic field has a duty-cycle of about 10 percent.

14. The method of claim 9, wherein the pulsing of the RE electric-magnetic field has a duty-cycle between about 1 percent and about 99 percent.

15. The method of claim 1, wherein the enclosure further contains an arc tube with a low-pressure gas and a low pressure vapor, the operating step being performed without exciting the low pressure gas and the low pressure vapor contained within the arc-tube.

16. The method of claim 1, further comprising the step of confining the electrical discharge to a narrow flame-like plasma.

17. The method of claim 1, wherein the high pressure gas is primarily molecular nitrogen.

18. The method of claim 1 further comprising the step of analyzing the emission spectrum of the discharge to determine the composition and impurity content of the gas.

19. A method of nondestructively analyzing the gaseous content of an enclosure at a pressure of at least 0.1 atm, said method comprising the steps of:
    generating an RE field with a helical coil resonator sufficient to effect a discharge in the gas;
    contacting the helical coil resonator to a dielectric wall of the enclosure to thereby generate a discharge in the gas contained therein; and,
    spectrally analyzing the discharge.

20. The method of claim 19 wherein the step of generating an RE field includes the step of applying RF power to the helical coil resonator so that the resonator generates a voltage in excess of one hundred times the voltage of the RE power applied thereto.

21. The method of claim 19 wherein the step of generating an RF field includes the step of applying RF power to the helical coil resonator so that the frequency of the RE power matches the resonant frequency of the helical coil resonator.

22. The method of claim 19 wherein the step of generating an RF field includes the step of applying RE power to the helical coil resonator so that the impedance of the RE power matches the input impedance of the helical coil resonator.

23. The method of claim 19 wherein the step of generating an RE field includes the step of applying RE power to the helical coil resonator so that the length of the helical coil is about one quarter of the wavelength of the RE power applied thereto.

24. The method of claim 19 wherein the step of spectrally analyzing the discharge includes the step of determining the presence of selected impurities.

25. The method of claim 24 wherein the selected impurities include one or more of oxygen, hydrogen, and carbon.

26. The method of claim 24 wherein the impurity concentration by volume is less than about 1 percent.

27. The method of claim 26 wherein the impurity concentration by volume is less than about 0.1 percent.

28. The method of claim 27 wherein the impurity concentration by volume is less than about 0.01 percent.

29. The method of claim 19 wherein the pressure of the gas is between about 0.1 atm and about 2.0 atm.

30. The method of claim 29 wherein the pressure of the gas is about 0.5 atm.

31. The method of claim 19 wherein the enclosure forms the outer jacket of a high intensity discharge lamp.

32. The method of claim 31 wherein the jacket contains nitrogen at a pressure of about 0.5 atm.

33. The method of claim 19 wherein the step of generating an RE field includes the step of applying RF power to the helical coil resonator at a frequency between about 100 kHz and 100 MHz.

34. The method of claim 33 wherein the step of generating an RE field includes the step of applying RE power to the helical coil resonator at a frequency of about 10 MHz.

35. The method of claim 19 wherein the step of generating an RE field includes the step of applying pulsed RE power to the helical coil resonator.

36. The method of claim 35 wherein the RE power is pulsed at a frequency between about 10 Hz and about 1000 Hz.

37. The method of claim 36 wherein the RE power is pulsed at a frequency of about 120 Hz.

38. The method of claim 35 wherein the RE power has a duty cycle between about 5% and about 20%.

39. The method of claim 38 wherein the RE power has a duty cycle of about 10%.

40. A system for generating a discharge in a high pressure gas comprising:
   a dielectric enclosure containing high pressure gas;
   an RE generator for generating an RE field sufficient to effect a discharge in the high pressure gas, said generator comprising:
      an RE power source; and
      a helical coil resonator, said resonator being connected at one end to said RE power source and forming an electrode at the other end thereof, said electrode being in contact with said dielectric enclosure to thereby establish a discharge in the gas contained therein.

41. The system of claim 40 further comprising means for spectrally analyzing the discharge generated in the high pressure gas.

42. The system of claim 41 wherein the dielectric enclosure comprises the outer jacket of an HID lamp containing a fill gas at a pressure of about 0.5 atm.

43. The system of claim 42 wherein the system detects the presence of hydrogen in the jacket at concentrations by volume of at least 0.1%.

44. The system of claim 42 wherein the system detects the presence of oxygen in the jacket at concentrations by volume of at least 0.3%.

45. The system of claim 40 wherein the frequency of the RE power source is matched with the resonance frequency of the helical coil resonator.

46. The system of claim 40 wherein the length of the helical coil in said helical coil resonator is about one fourth of the wavelength of the RF power provided by said RE power source.

47. The system of claim 40 wherein the voltage at the electrode of said helical coil resonator is at least 50 times greater than the voltage of the RE power source.

48. The system of claim 47 wherein the voltage at the electrode of said helical coil resonator is at least 100 times greater than the voltage of the RE power source.

49. A method of generating an electrical discharge in a high pressure gas contained in a sealed enclosure, the method comprising the steps of:
   contacting an electrode of a helical coil resonator with a dielectric wall of the enclosure, wherein the longitudinal axis of the helical coil is substantially normal to the surface of the dielectric wall where the electrode contacts the dielectric wall, and
   driving the helical coil resonator at an RE frequency to generate an RE electric-magnetic field to thereby generate an capacitive discharge in the high pressure gas.

50. A method of nondestructively analyzing the gaseous content of an enclosure forming the outer jacket of a high intensity discharge lamp at a pressure of at least 0.1 atm, said method comprising the steps of:
   generating an RE field with a helical coil resonator sufficient to effect a capacitive discharge in the gas;
   contacting the an electrode of the helical coil resonator to a dielectric wall of the enclosure to thereby generate a discharge in the gas contained therein; and
   spectrally analyzing the discharge to thereby determine the gaseous content.

51. A system for generating a discharge in a high pressure gas comprising:
   a dielectric enclosure containing high pressure gas;
   an RF generator for generating an RF field sufficient to effect a discharge in the high pressure gas, said generator comprising:
      an RF power source; and
      a helical coil resonator comprising a conductive shield concentric with a wire helix, said wire helix being connected at one end to said RE power source and forming an electrode at the other end thereof, said conductive shield being grounded proximate to the one end and said electrode being in contact with said dielectric enclosure to thereby establish a discharge in the gas contained therein.

52. A method of nondestructively analyzing the gaseous content of an enclosure at a pressure of at least 0.1 atm, said method comprising the steps of:
   contacting the electrode of a helical coil resonator to a dielectric wall of the enclosure;
   generating an RE field with the helical coil resonator sufficient to effect a time varying peak electric field through the dielectric wall proximate to the electrode and generate a discharge in the gas; wherein the direction of the peak electric field is directed radially from the electrode; and,
   spectrally analyzing the discharge to thereby determine the gaseous content.

* * * * *